United States Patent
Buettner-Janz et al.

(10) Patent No.: US 10,098,750 B2
(45) Date of Patent: Oct. 16, 2018

(54) PROSTHETIC INTERVERTEBRAL DISK

(71) Applicant: ulrich GmbH & Co. KG, Ulm (DE)

(72) Inventors: Karin Buettner-Janz, Berlin (DE);
Nelli Ruediger, Neu-Ulm (DE)

( * ) Notice: Subject to any disclaimer, the term of this patent is extended or adjusted under 35 U.S.C. 154(b) by 0 days.

(21) Appl. No.: 14/473,780

(22) Filed: Aug. 29, 2014

(65) Prior Publication Data

US 2014/0371856 A1  Dec. 18, 2014

Related U.S. Application Data

(63) Continuation of application No. 13/365,308, filed on Feb. 3, 2012, now abandoned.
(Continued)

(30) Foreign Application Priority Data

May 18, 2011 (DE) .......... 10 2011 050 453

(51) Int. Cl.
*A61F 2/44* (2006.01)
*A61F 2/30* (2006.01)

(52) U.S. Cl.
CPC ........ *A61F 2/4425* (2013.01); *A61F 2/30965* (2013.01); *A61F 2002/304* (2013.01); *A61F 2002/3008* (2013.01); *A61F 2002/30014* (2013.01); *A61F 2002/30016* (2013.01); *A61F 2002/30056* (2013.01); *A61F 2002/30365* (2013.01); *A61F 2002/30369* (2013.01); *A61F 2002/30385* (2013.01);
(Continued)

(58) Field of Classification Search
CPC .......... A61F 2/44; A61F 2/442; A61F 2/4425; A61F 2002/443
See application file for complete search history.

(56) References Cited

U.S. PATENT DOCUMENTS 3,495,272 A * 2/1970 Tempelhof ............. A42B 3/127
2/181.4
3,958,278 A  5/1976 Lee
(Continued)

FOREIGN PATENT DOCUMENTS

CN  1387423 A  12/2002
EP  0 317 972  5/1989
(Continued)

*Primary Examiner* — Kevin T Truong
*Assistant Examiner* — Tracy Kamikawa
(74) *Attorney, Agent, or Firm* — 24IP Law Group; Timothy R DeWitt

(57) ABSTRACT

An intervertebral disk prostheses for the total replacement of an intervertebral disk of the lumbar and cervical spine has an upper plate having upwardly projecting formations anchoring it to an upper vertebra on its upper face and a concavity on its inner face surrounded by an edge. A lower plate is provided with downwardly projecting formations anchoring it to a lower vertebra on its lower face and a flat inner face surrounding a groove extending front-to-back. A middle plate between the upper and lower plate has on its upper face a convexity that is identically or differently shaped to the concavity on the inner face of the upper plate and a ridge extending front-to-back surrounded by a flat lower face of the middle plate. The ridge has flanks and the groove houses the ridge of the middle plate and permits the ridge to slide front-to-back in the groove.

15 Claims, 4 Drawing Sheets

Related U.S. Application Data

(60) Provisional application No. 61/507,498, filed on Jul. 13, 2011.

(52) U.S. Cl.
CPC ........... *A61F 2002/30387* (2013.01); *A61F 2002/30397* (2013.01); *A61F 2002/30614* (2013.01); *A61F 2002/30616* (2013.01); *A61F 2002/30662* (2013.01); *A61F 2002/30795* (2013.01); *A61F 2002/30807* (2013.01); *A61F 2002/30813* (2013.01); *A61F 2002/30822* (2013.01); *A61F 2002/30823* (2013.01); *A61F 2002/30827* (2013.01); *A61F 2002/30841* (2013.01); *A61F 2002/30843* (2013.01); *A61F 2002/30935* (2013.01); *A61F 2002/443* (2013.01); *A61F 2310/00023* (2013.01); *A61F 2310/00029* (2013.01); *A61F 2310/00059* (2013.01); *A61F 2310/00131* (2013.01); *A61F 2310/00161* (2013.01); *A61F 2310/00167* (2013.01); *A61F 2310/00179* (2013.01); *A61F 2310/00287* (2013.01)

(56) References Cited

U.S. PATENT DOCUMENTS

| | | | |
|---|---|---|---|
| 4,412,793 A | 11/1983 | Stenberg et al. | |
| 5,108,442 A | 4/1992 | Smith | |
| 5,258,031 A | 11/1993 | Salib | |
| 5,306,307 A | 4/1994 | Senter | |
| 5,370,697 A | 12/1994 | Baumgartner | |
| 6,368,350 B1 * | 4/2002 | Erickson | A61F 2/4425 623/17.11 |
| 7,517,363 B2 * | 4/2009 | Rogers | A61F 2/4425 623/17.11 |
| 2003/0176923 A1 | 9/2003 | Keller et al. | |
| 2004/0002761 A1 | 1/2004 | Rogers et al. | |
| 2005/0060034 A1 | 3/2005 | Berry et al. | |
| 2005/0085917 A1 | 4/2005 | Marnay et al. | |
| 2006/0190082 A1 * | 8/2006 | Keller | A61F 2/4425 623/17.11 |
| 2008/0009948 A1 | 1/2008 | Amin et al. | |
| 2008/0161921 A1 | 7/2008 | Carls et al. | |
| 2008/0161932 A1 | 7/2008 | Armstrong et al. | |
| 2008/0215156 A1 | 9/2008 | Duggal et al. | |
| 2009/0082867 A1 | 3/2009 | Bueno et al. | |

FOREIGN PATENT DOCUMENTS

| | | |
|---|---|---|
| EP | 0 512 529 | 11/1992 |
| EP | 0 566 810 | 10/1993 |
| FR | 2 632 516 | 12/1989 |
| FR | 2 718 635 A1 | 10/1995 |
| WO | 91 13598 | 9/1991 |
| WO | 93 01771 | 2/1993 |
| WO | 0115638 | 3/2001 |
| WO | 2008/036502 A1 | 3/2008 |

\* cited by examiner

PROSTHETIC INTERVERTEBRAL DISK

CROSS REFERENCE TO RELATED APPLICATIONS

This application is a continuation of U.S. patent application Ser. No. 13/365,308, filed Feb. 3, 2012, which claims the priority of German patent application 10 2011 050 453 filed May 18, 2011 and claims the benefit of the filing of U.S. provisional application 61/507,498 filed Jul. 13, 2011.

BACKGROUND OF THE INVENTION

Field of the Invention

The present invention relates to an intervertebral disk prosthesis. More particularly this invention relates to a three-part intervertebral disk prosthesis for the total replacement of an intervertebral disk of the cervical and lumbar spine.

Brief Description of the Related Art

An intervertebral disk prosthesis has at least a lower plate and an upper plate having anchor formations on their sides facing toward the adjacent vertebral bodies in case of a two-part prosthesis. A three-part-prosthesis comprises further an intermediate or middle plate. Neighboring plates articulate via their surfaces that get in contact. Thus, the parts of an intervertebral disk prosthesis are also designated as sliding partners, wherein the intermediate sliding partner arranged between upper and lower sliding partner represents an intermediate sliding plate.

The U.S. Patent Application Publication No. 2009/0082867 A1 of Bueno et al discloses a prosthesis with basically 3 articulating sliding partners, in which the intermediate sliding partner has no function for keeping the central distance between the upper and lower plate. Upper and lower sliding partner have both spherical convex inner surfaces, which are identical with the exception that the upper convexity has a hole housing a pivot of the lower sliding partner, wherein the pivot ends in a sphere. An intermediate partner having a central opening is arranged between the inner surfaces of upper and lower sliding partner. The surfaces of the intermediate partner facing the inner surfaces of upper and lower sliding partner are concave-shaped. The clearance between central opening of the intermediate partner and the pivot of the lower sliding partner may be dimensioned with one value for the anterior-posterior direction of the vertebral segment and another value for the lateral direction of the vertebral segment. A prosthesis according to US 2009/0082867 A1 has no means for limiting rotation around the vertical body axis and comprises only curved articulation surfaces. Further the pivot in the hole is directly limiting the range of extension and flexion as well as the range of lateral bending to both sides.

SUMMARY OF THE INVENTION

It is therefore an object of the present invention to provide a functional total intervertebral disk prosthesis, providing the possibility to adjust physiological motion in anterior-posterior and both lateral directions as well as rotation around the vertical body axis in a first sliding area and front-to-back translation in a second sliding area, wherein a slip out of an intermediate sliding plate is prevented.

The present disclosure provides an intervertebral disk prosthesis for the total replacement of an intervertebral disk of the cervical or lumbar spine, comprising an upper plate having upwardly projecting formations anchoring it to an upper vertebra on its upper surface and a concavity on its lower inner surface surrounded by an edge, a lower plate provided with downwardly projecting formations anchoring it to a lower vertebra on its lower surface and a flat upper inner surface surrounding a guide groove extending front-to-back with a first body stop on the back and/or a second body stop on the front, an intermediate sliding plate arranged between the upper and lower plate having on its upper surface a convexity, which is equally or different shaped to the concavity on the lower inner surface of the upper plate, and a guide ridge having flanks on its flat lower surface, extending front-to-back, wherein the guide groove of the lower plate houses the guide ridge of the intermediate sliding plate permitting the guide ridge to slide front-to-back within the guide groove as straight-line motion, while in the sliding area of the convexity of the intermediate sliding plate and of the concavity of the upper plate limited extension, flexion, lateral bending to right and left side, and axial rotation to both sides takes place.

It is an advantage of a total disk prosthesis according to the present disclosure that the guide ridge cannot be released from the guide groove, preventing a slip-out of the intermediate sliding plate, so-called luxation, without using an instrument. The guide ridge surface will be pressed against the flank surfaces of the guide groove and the guide ridge is thus retained in the guide groove. The movable link between the flat upper inner surface of the lower plate and the flat lower surface of the intermediate sliding plate enables a limited straight-line movement of the intermediate sliding plate in the dorso-ventral direction limited by the first body stop and/or by the second body stop to mimic sagittal straight-line motion. In context of the description of this invention and in the claims the term>sagittal view=will be used as a by-word for>side view=. Each of them can be used synonymic. The sagittal view is the left or the right side view of the spine, the vertebrae and the total disk prosthesis.

In order to provide a defined straight-line motion or straight-line guidance, it is useful if a dovetail guide having a V-formation or a T-section formation is provided between the guide ridge and the guide groove. The V-formation or the T-section formation are preferably built upside down within the lower plate. Basically the end of the guide ridge has a larger dimension than its stem, which is directly connected to the flat lower surface of the intermediate sliding plate, to prevent a slip out of the guide ridge out of the guide groove.

It is an advantage that a combined motion of the sliding partners is possible resulting from the limited straight-line movement of the lower surface of the intermediate sliding plate and the upper inner surface of the lower plate constituting the straight-line sliding motion in dorso-ventral direction, and the limited articulation between the convexity of the upper surface of the intermediate sliding plate and the concavity of the lower inner surface of the upper plate. Thus, the range of motion along the three body axes can be adjusted to the situation of the respective intervertebral space, including as coupled motion. In other words, consequently its motion results in a superposition of a linear translational sliding motion in the dorso-ventral direction, and of an inclination provided by the convexity in connection with the corresponding concavity resulting in flexion, in extension, in lateral bending, and in axial soft limited rotation.

It is an advantage if the guide ridge is formed integrally with the intermediate sliding plate or is connected to the intermediate sliding plate as a separate part. When the guide ridge is formed as a separate part, this provides the possibility of producing the guide ridge from the same or a different material as the intermediate sliding plate. Like the intermediate sliding plate, the guide ridge can then be made of a material that exhibits a low friction contact with the material of the lower plate. The guide ridge can be connected to the intermediate sliding plate in a conventional manner, for example by a snap closure or a screwed connection. In case, the guide ridge is formed integrally with the intermediate sliding plate, both components can be produced in a single production step and the guide ridge becomes an inherent part of the intermediate sliding plate.

It is also possible to use the upper plate as a lower plate and the corresponding lower plate as an upper plate, so that the articulating parts of the disk prosthesis are configured "upside down". It is further intended that parts of the prosthesis are made of different material or even the same material with different properties.

A further embodiment is characterized in that the guide groove is embodied within the intermediate sliding plate and the guide ridge is assigned to the lower plate. Or the guide ridge is assigned to the upper plate, in case that the upper plate has a flat lower inner surface and the intermediate sliding plate has an upper flat surface with a guide groove, and a concavity is on the upper inner surface of the lower plate articulating with the convexity of the lower surface of the intermediate sliding plate. Here, too, the material selection of the individual components can lead to defined sliding properties of the intervertebral disk prosthesis.

It has proven to be particularly favorable if in sagittal view the intermediate sliding plate and/or the upper plate and/or the lower plate is angled. The tilt angle of the upper plate with respect to the lower plate can be restricted in a manner as elucidated hereafter. In case the upper plate is angled, it is favorable, that the concavity of the upper plate surrounds the corresponding convexity of the intermediate sliding plate in a larger range. This leads to a better stability of the prosthesis in the area of free motion between the concavity and the convexity. Further it is possible to choose predetermined angles in sagittal view for the plates to prevent a segmental kyphosis. It is also possible to provide a stop or counterstop on the surface of the intermediate sliding plate for interaction with a counterstop or stop embodied on the inner surface of the upper plate.

In order to recreate the motion of a functional intervertebral disk as precisely as possible, it has proven to be favorable for the intermediate sliding plate to have a convexity and the upper plate or the lower plate to have a corresponding concavity each with a design of sliding surfaces for having physiological range of motion in extension, flexion, lateral bending to right and left as well as in axial rotation to right and left.

It has also proven to be favorable, that the intervertebral disk prosthesis comprises a plurality of guide grooves and a corresponding plurality of guide ridges. This increases the stability of the prosthesis, which is especially needed for prostheses inserted between lumbar vertebrae. Moreover, an even stronger bond between the guide ridge and the guide groove is produced and thus an even better guided motion of the intermediate sliding plate is provided.

In order for it to be possible to adapt optimally to the conditions of the position chosen in the spine, it has proven to be useful for the convexity and the concavity to be offset in the dorsal direction, resulting in the displacement of the center of rotation in dorsal direction.

It is particularly favorable if the intermediate sliding plate is replaceable. This provides the option of revision for insertion of a different intermediate sliding plate. If the guide ridge is thereby detachably connected to the intermediate sliding plate, the replacement thereof can also be carried out after insertion of the guide ridge into the guide groove. In case the guide ridge is non-detachably connected to the intermediate sliding plate, for the removal of the intermediate sliding plate from the lower plate or the upper plate an instrument is needed. As precondition a slight elastic material of the intermediate sliding plate and/or a slit in the guide ridge is needed to connect the intermediate sliding plate with the lower plate or the upper plate. In this preferred embodiment the guide ridge can be deformed elastically, to build a secure connection between the guide ridge and the guide groove.

It is advantageous if the lower plate and/or the upper plate have at least one, preferably two tool guides. This makes it easier for a surgeon to insert the intervertebral disk prosthesis between the two vertebral bodies. Other well-known intervertebral disk prostheses, such as the M6-prosthesis, have to be destroyed before they can be removed. With these tool guides it is possible to remove, and if necessary to reinsert, the same intervertebral disk prosthesis without damaging or even destroying it.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

The above and other objects, features, and advantages will become more readily apparent from the following description without being limited to the disclosed embodiments, reference being made to the accompanying drawing in which.

DETAILED DESCRIPTION

Figure 1:
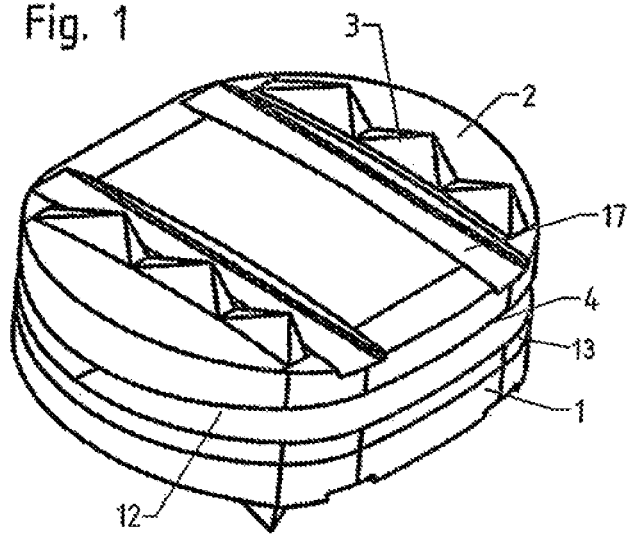
FIG. 1 is a perspective view of an intervertebral disk prosthesis according to the invention.

As seen in FIGS. 1-5 an intervertebral disk prosthesis has a lower plate 1 and an upper plate 2 having outer surfaces directed outwardly toward the respective flanking (unillustrated) vertebrae and each carrying anchor formations 3. An intermediate sliding plate 13 is provided between the lower plate 1 and the upper plate 2. At the intermediate sliding plate 13 there is formed a convexity 4 which faces the concave lower inner surface of the upper plate 2. A guide ridge 5 projecting downward from the intermediate sliding plate 13 is shiftable in a front-to-back or dorso-ventral direction in a similarly extending but upwardly open guide groove 7 formed in the lower plate 1.

The guide ridge 5 has a pair of oppositely laterally directed side surfaces or flanks 8 each having an outwardly projecting lower edge formation 9. The guide groove 7 similarly has a pair of confronting laterally inwardly directed side surfaces or flanks 6 each having an inwardly projecting upper edge formation 10. Thus the guide ridge 5 is captured in the guide groove 7 and, while it can slide front-to-back in the guide groove 7, it cannot be pulled upwardly out of the guide groove 7.

Figure 2:
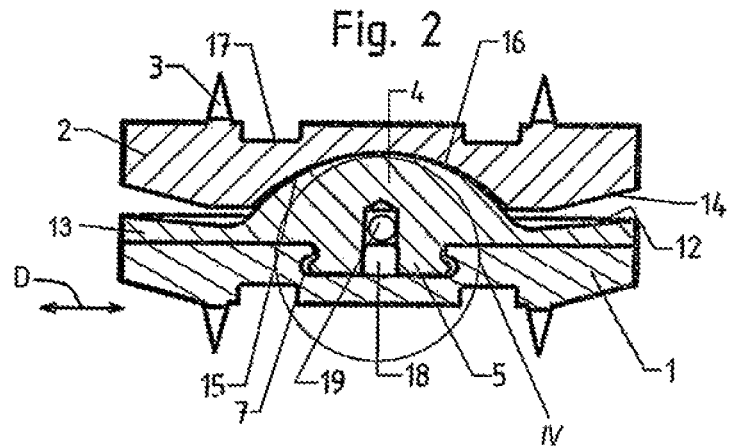
FIG. 2 is a front view partly in section through the FIG. 1 disk.

In FIGS. 1 and 2 the anchor formations 3 are vertically projecting saw teeth. In addition the outer surfaces of the lower plate 1 and the upper plate 2 are formed with vertically open tool guides 17 that allow the implant to be fitted to a four-prong implant tool for installation. With these tool guides 17 it is possible to remove, and if necessary to reinsert, the same intervertebral disk prosthesis without damaging or even destroying it. In this embodiment the intermediate sliding plate 13 and the upper plate 2 are angled. The angles can be similar or different.

Figure 3:
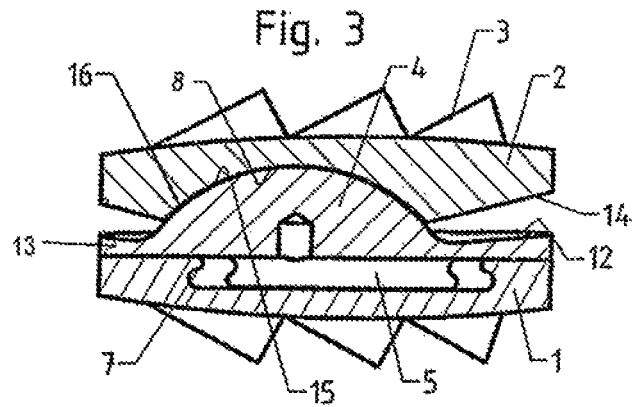
FIG. 3 is a sagittal view partly in section of the disk.

FIG. 3 shows that the intermediate sliding plate 13 formed on the top surface of the intermediate sliding plate 13 has an upwardly convexity 4 with a smooth upper surface 15 and the upper plate 2 has a concavity 8 with a complementary downwardly concave lower inner surface 16. The surfaces 15 and 16, seen in sagittal view, are of same or different shape. In addition the surfaces 15 and 16 are offset from the centers of the plates 1 and 2 dorsally or toward the rear (the left in FIG. 3), and the surrounding annular surfaces 12 and 14 are correspondingly radially formed wider in ventral direction.

In sagittal view the upper surface of the upper plate 2 and the lower surface of the lower plate 1 are formed slightly convex toward the unillustrated vertebral bodies, and in plan view they form a virtually round and thus compact intervertebral disk prosthesis. Furthermore, it is conceivable to embody the intervertebral disk prosthesis in a kidney-shaped manner or with another preferred shape.

With regard to the material selection, it is usual to use the lower plate 1 and the upper plate 2 of titanium, titanium alloys or titanium carbide, alloys of cobalt and chromium or other suitable metals, tantalum or suitable tantalum compounds, suitable ceramic materials, plastics, diamond, carbon or composite materials. Often the inner surfaces of the lower plate 1 and the upper plate 2 and the surfaces of the intermediate sliding plate 13 are mirror-polished in order to minimize wear. However, it has proven to be favorable for the intermediate sliding plate 13 including its convexity 4 and its guide ridge 5 to be made from polyethylene, although other elastically deformable materials with similar properties or combinations thereof can also be used.

The intermediate sliding plate 13 is centrally formed with a recess in which at least one tantalum ball 19 is held to facilitate x-ray imaging of the installed implant. The ball 19 can be of any other non-radiolucent material, too. It is also within the scope of the invention that the parts of the prosthesis comprise other radiolucent tags for x-ray imaging. Furthermore the intermediate sliding plate 13 is formed within the center of its guide ridge 5 with a downwardly open and longitudinally extending slit 18 that facilitates snapping the elastically deformable guide ridge 5 into the guide groove 7 in the much harder lower plate 1. This slit 18 can be dispensed with when the material of the guide ridge 5 is sufficiently compressible to allow assembly of the implant.

FIGS. 4a to 4f show further possible connections between the guide ridge 5 and the guide groove 7.

Figure 4:
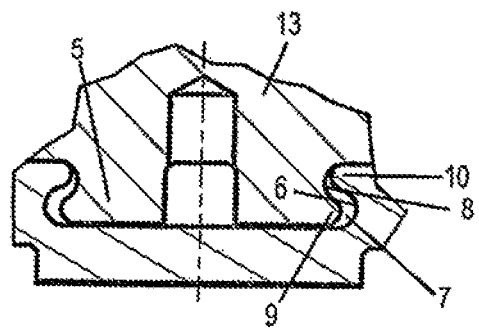
FIG. 4 is a large-scale view of the detail shown at IV in FIG. 2.
Figure 4A:
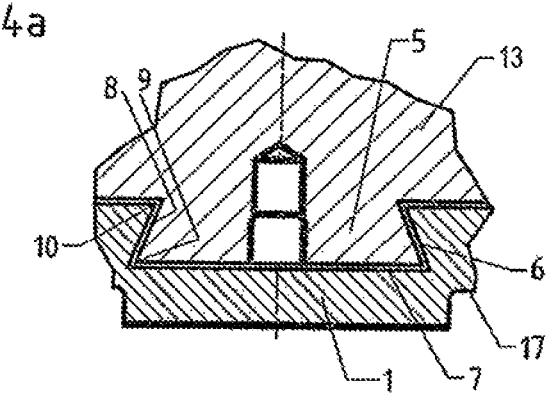
FIGS. 4a - 4f are views like FIG. 4 but showing different embodiments of the guide formations of the invention.

FIG. 4a shows a dovetail guide ridge 5 and a complementary dovetail guide groove 7.

Figure 4B:
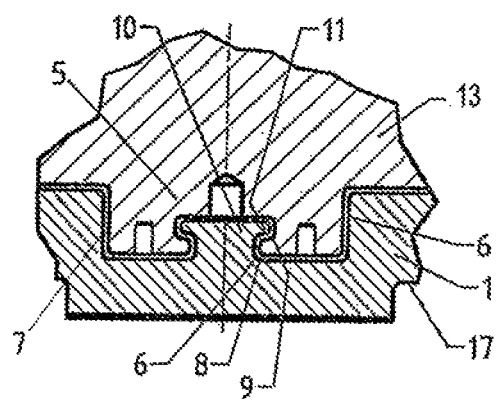

In FIG. 4b a T-section guide ridge 10 with rounded corners formed on the lower plate 1 engages upward into a complementary T-section guide groove 11 formed in the guide ridge 5.

Figure 4C:
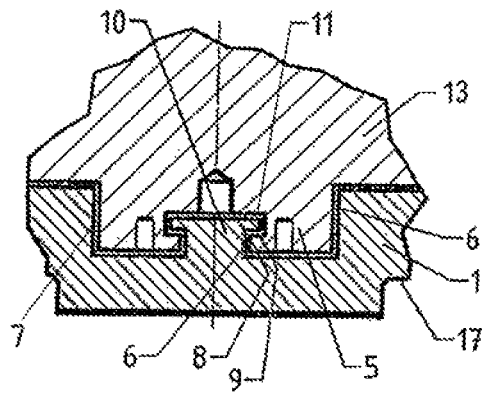

FIG. 4c shows a T-section guide ridge 10 with sharp edges engaged in a complementary T-section guide groove 11 of a guide ridge 5.

Figure 4D:
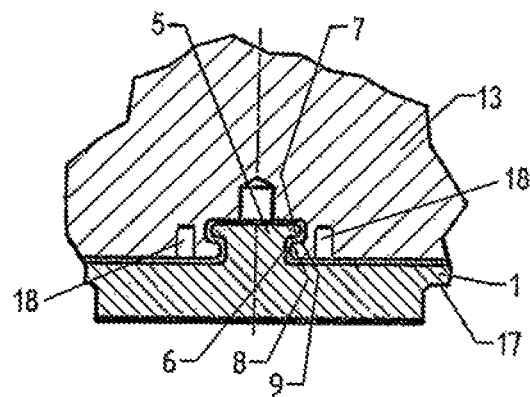

FIG. 4d shows additionally that the connection between the guide ridge 5 and the guide groove 7 can also be built the other way round, what is covered by the scope of the invention, too. The guide groove 7 is formed in the intermediate sliding plate 13 and the corresponding guide ridge 5 is integrally formed with or detachably connected to the lower plate 1. Here, in the intermediate sliding plate 13 a pair of the relief slits 18 flanks the guide ridge 5 of the lower plate 1 to allow the intermediate sliding plate 13 to be snapped onto it.

Figure 4E:
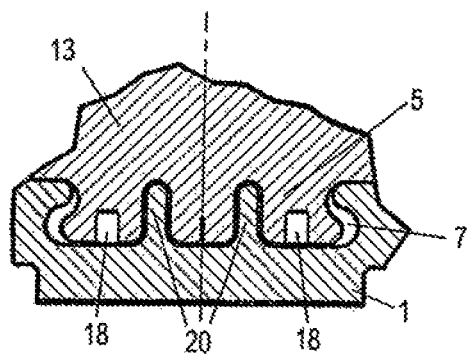

FIG. 4e shows a pair of slits 18 formed in the guide ridge 5 of the intermediate sliding plate 13 while a pair narrow guide rails 20 formed in the guide groove 7 on the lower plate 1 engage upward into complementary guide slots in the guide ridge 5 to ensure good front-to-back guidance as sagittal straight-line motion.

Figure 4F:
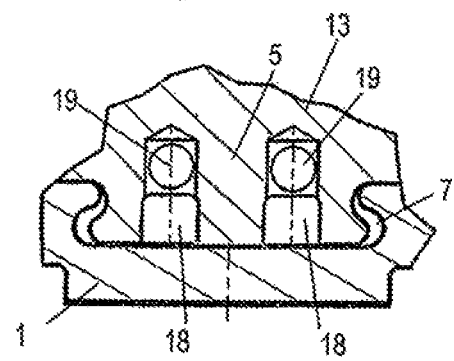

FIG. 4f shows a pair of slits 18 in the guide ridge 5 with respective tantalum balls 19 seated above them.

Often a rather rounded, semicircular or curved shape of the connection of the guide ridge 5 with the guide groove 7 is useful, since corners and edges are more susceptible to losses of stability of these connections in terms of material technology.

Figure 5:
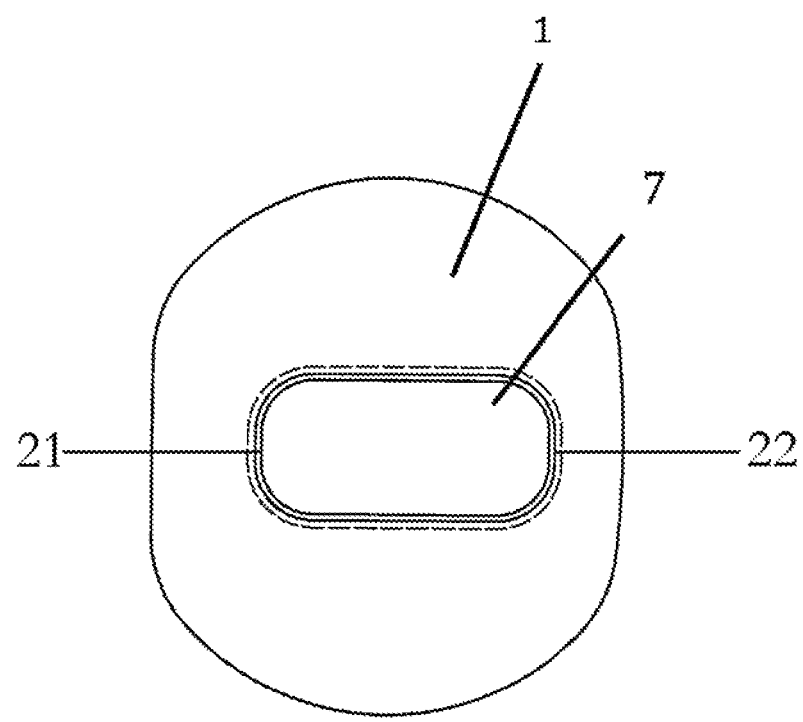
FIG. 5 shows the inner surface of the lower plate including the first body stop on the back and the second body stop on the front.

FIG. 5 shows the upper inner surface of the lower plate 1 with the guide groove 7. The surrounding of the guide groove protrudes, which is indicated by the dotted line so that the surrounding encloses the projecting portions of the guide ridge 5. The figure also shows that the sagittal straight-line motion is limited by a first body stop 21 in dorsal direction or the back and by a second body stop 22 in ventral direction or the front. These body stops 21, 22 are positioned at or form the ends of the guide groove 7 and they interact with the guide ridge 5 which slides within the guide groove 7.

Here it is also possible to form the guide groove 7 with only the first body stop 21 or only the second body stop 22. Then, a slot or an opening arises at the front or the back of the lower plate 1 allowing an easier mounting of the intermediate sliding plate 13 to the lower plate 1. This opening results in the guide groove 7 being opened to the front which is also advantageous in case the intermediate sliding plate 13 has to be removed. This has to be done when the intermediate sliding plate 13 is damaged or another size is needed. The old intermediate sliding plate 13 can pass through the opening on the front of the lower plate 1 and another new intermediate sliding plate 13 can be inserted between lower plate 1 and upper plate 2.

Another inherent advantage is given due to the use of an intermediate sliding plate 13 which is not built of an elastically deformable material, for example other than polyethylene. The intermediate sliding plate 13 can be built of a hard material that leads to other sliding properties between the intermediate sliding plate 13 and the lower plate 1 and/or between the intermediate sliding plate 13 and the upper plate 2. Even the properties of the lower plate 1 and/or the upper plate 2 can be altered to result in different and improved material pairing.

For the relative straight-line motion between the intermediate sliding plate 13 and the lower plate 1, it is sufficient that a minimal clearance is provided between the surfaces of guide ridge 5 and the guide groove 7. Then, of course, also the flat lower surface of the intermediate sliding plate 13 and the flat upper inner surface of the lower plate 1 are shaped adequately to allow this straight-line motion.

To close the opening after insertion of an intermediate sliding plate 13, a covering cap is provided. This covering cap can then be used as a body stop that limits the straight-line motion of the guide ridge 5 within the guide groove 7 on its own. Preferably the covering cap is detachable or removable mounted to the opening within the lower plate 1, whereas the connection is built in a conventional manner, for example by a snap closure or a screwed connection.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the above-described documents is incorporated by reference herein.

What is claimed is:

1. An intervertebral disk prosthesis for the total replacement of an intervertebral disk of the lumbar and cervical spine, the prosthesis comprising
    an upper plate having an upper face formed with upwardly projecting formations for anchoring the upper plate to an upper vertebra and a lower face formed with a concavity surrounded by a first annular surface that extends to meet an outwardly facing circumferential surface of the upper plate at an outer edge of the first annular surface, wherein said first annular surface is angled toward said upper face of said upper plate around its entire circumference in a radial direction away from the concavity and to the outer edge of the first annular surface;
    a lower plate having a lower face formed with downwardly projecting formations for anchoring the lower plate to a lower vertebra and a flat upper inner face forming and surrounding at least one guide groove that extends front-to-back; and
    an intermediate sliding plate arranged between the upper and lower plates having a flat lower face and having an upper face formed with a convexity surrounded by a second annular surface that extends to meet an outwardly facing circumferential surface of the intermediate sliding plate at an outer edge of the second annular surface, wherein said second annular surface is angled away from said lower face of said intermediate sliding plate around its entire circumference in a radial direction away from the convexity and to the outer edge of the second annular surface, wherein said flat lower face is formed with and surrounds at least one guide ridge having flanks, extending front-to-back, and engaging in the at least one guide groove of the lower plate in such a manner that the at least one guide ridge can slide in a straight line between front and back in the at least one guide groove, and the at least one guide ridge is made of a semi-elastic composition and is formed with at least one open slit so that the at least one guide ridge can be elastically deformed and fitted into the respective at least one guide groove,
    wherein the convexity of the intermediate sliding plate engages the concavity of the upper plate and the first annular surface engages the second annular surface to permit limited ranges of motion of the upper plate relative to the intermediate sliding plate.

2. The prosthesis of claim 1, wherein the at least one guide ridge of the intermediate sliding plate ends with outwardly projecting portions next to the open slit and the at least one guide groove of the lower plate has inwardly projecting formations that enclose and capture the portions of the respective at least one guide ridge, so that the intermediate sliding plate cannot be separated from the lower plate without compression of the open slit.

3. The prosthesis of claim 1, wherein the at least one guide groove and the at least one guide ridge are of complementary dovetail or T-section shape with sharp corners.

4. The prosthesis of claim 1, wherein the at least one guide groove and the at least one guide ridge are of dovetail or T-section shape with rounded corners.

5. The prosthesis defined of claim 1, wherein the at least one guide ridge each comprise a stem and an outer end of the at least one guide ridge has a larger dimension than the stem.

6. The prosthesis of claim 1, wherein at least two of the lower plate, the upper plate, the intermediate sliding plate and the at least one guide ridge are made of different material or the same material with different properties.

7. The prosthesis of claim 1, wherein the lower plate is formed in the at least one guide groove with narrow guide rails that fit in complementary guide slots in the respective at least one guide ridge for guiding of the at least one guide ridge in the at least one guide groove.

8. The prosthesis of claim 1, wherein the lower plate comprises at least one T-section guide ridge and the intermediate sliding plate comprises at least one respective complementary T-section guide groove.

9. The prosthesis of claim 1, wherein at least one of the plates comprises an imaging ball of tantalum or another non-radiolucent material.

10. The prosthesis of claim 1, wherein the upper and lower plates are formed on their outer surfaces with tool guides for implantation or explantation.

11. The prosthesis of claim 1, wherein the intermediate sliding plate is exchangeable during revision surgery.

12. The prosthesis of claim 1, wherein in sagittal view the intermediate sliding plate or the upper plate or the lower plate is angled.

13. The prosthesis of claim 12, wherein the angle of the intermediate sliding plate or the upper plate or the lower plate is selected to avoid kyphosis in the spinal segment comprising the intervertebral disk to be replaced.

14. The prosthesis of claim 1, wherein the at least one guide groove of the lower plate is formed with an opening.

15. The prosthesis of claim 14, wherein the opening is closed by a detachable covering cap.

* * * * *